US010473627B2

(12) United States Patent
McGovern et al.

(10) Patent No.: US 10,473,627 B2
(45) Date of Patent: Nov. 12, 2019

(54) PORTABLE ACOUSTIC APPARATUS FOR IN-SITU MONITORING OF A WORKPIECE

(71) Applicant: GM GLOBAL TECHNOLOGY OPERATIONS LLC, Detroit, MI (US)

(72) Inventors: Megan E. McGovern, Troy, MI (US); Teresa J. Rinker, Royal Oak, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 225 days.

(21) Appl. No.: 15/499,955

(22) Filed: Apr. 28, 2017

(65) Prior Publication Data

US 2018/0313791 A1 Nov. 1, 2018

(51) Int. Cl.
*G01N 29/11* (2006.01)
*G01N 29/07* (2006.01)
*G01N 29/28* (2006.01)

(52) U.S. Cl.
CPC .............. *G01N 29/28* (2013.01); *G01N 29/07* (2013.01); *G01N 29/11* (2013.01); *G01N 2291/0289* (2013.01); *G01N 2291/044* (2013.01); *G01N 2291/102* (2013.01)

(58) Field of Classification Search
CPC ........ G01N 29/28; G01N 29/11; G01N 29/07; G01N 2291/102; G01N 2291/044; G01N 2291/0289
USPC .......................................................... 73/579
See application file for complete search history.

(56) References Cited

U.S. PATENT DOCUMENTS

| 3,198,489 | A | * | 8/1965 | Finch | B06B 1/0618 |
| | | | | | 134/1 |
| 4,561,291 | A | * | 12/1985 | Ainlay | G01M 3/3245 |
| | | | | | 73/302 |
| 5,191,327 | A | | 3/1993 | Talmadge et al. | |
| 5,214,616 | A | * | 5/1993 | Terhune | G01N 29/223 |
| | | | | | 367/96 |
| 5,255,565 | A | | 10/1993 | Judd et al. | |
| 5,665,141 | A | * | 9/1997 | Vago | B08B 3/12 |
| | | | | | 422/20 |
| 5,687,391 | A | | 11/1997 | Judd et al. | |
| 5,796,003 | A | | 8/1998 | Sandhu et al. | |
| 6,049,411 | A | | 4/2000 | Sandhu et al. | |
| 6,160,621 | A | * | 12/2000 | Perry | G01B 11/0683 |
| | | | | | 250/559.27 |

(Continued)

*Primary Examiner* — Jacques M Saint Surin
(74) *Attorney, Agent, or Firm* — Quinn IP Law

(57) ABSTRACT

An apparatus for in-situ monitoring of a workpiece includes a fluidic container defining a cavity and having a peripheral portion that defines an aperture. The fluidic container contains an acoustic transmission fluid. A conformable membrane is sealably disposed about the peripheral portion of the aperture of the fluidic container. The conformable membrane is disposed to sealably contain the acoustic transmission fluid within the fluidic container and to conform to a surface of a portion of the workpiece absent an interposed fluid. An acoustic source transducer is disposed in the cavity of the fluidic container and in contact with the acoustic transmission fluid. The acoustic source transducer is disposed to generate a first acoustic wave in the direction of the workpiece. An acoustic receiving transducer is disposed to monitor a residual acoustic wave that is reflected from the workpiece in response to the first acoustic wave.

20 Claims, 3 Drawing Sheets

(56) References Cited

U.S. PATENT DOCUMENTS

| | | | |
|---|---|---|---|
| 6,536,553 B1 * | 3/2003 | Scanlon | G01N 29/069 181/108 |
| 7,284,434 B1 * | 10/2007 | Fleming | G01N 29/07 73/644 |
| 7,333,898 B2 * | 2/2008 | Griess | H04Q 9/00 702/35 |
| 7,367,236 B2 * | 5/2008 | Georgeson | G01M 5/0016 73/12.09 |
| 7,685,878 B2 * | 3/2010 | Brandstrom | G01B 21/047 376/249 |
| 8,255,180 B2 | 8/2012 | Sandhu | |
| 2011/0108181 A1 | 5/2011 | Cai et al. | |
| 2014/0116144 A1 | 5/2014 | Fetzer et al. | |

* cited by examiner ion acoustic monitoring device that is shown with reference to FIG. 1, in accordance with the disclosure;
PORTABLE ACOUSTIC APPARATUS FOR IN-SITU MONITORING OF A WORKPIECE

INTRODUCTION

Evaluation devices and methods may employ ultrasonic or other acoustic signals.

SUMMARY

An apparatus for in-situ monitoring of a workpiece is described, and includes a fluidic container defining a cavity and having a peripheral portion that defines an aperture. The fluidic container contains an acoustic transmission fluid. A conformable membrane is sealably disposed about the peripheral portion of the aperture of the fluidic container. The conformable membrane is disposed to sealably contain the acoustic transmission fluid within the fluidic container and to conform to a surface of a portion of the workpiece absent an interposed fluid. An acoustic source transducer is disposed in the cavity of the fluidic container and in contact with the acoustic transmission fluid. The acoustic source transducer is disposed to generate a first acoustic wave in the direction of the workpiece. An acoustic receiving transducer is disposed to monitor a residual acoustic wave that is reflected from the workpiece in response to the first acoustic wave.

An aspect of the disclosure includes the acoustic receiving transducer being an acoustography sensor.

Another aspect of the disclosure includes the acoustic receiving transducer being a multi-element acoustic receiving transducer.

Another aspect of the disclosure includes the acoustic receiving transducer being disposed in the same fluidic container as the acoustic sending unit.

Another aspect of the disclosure includes the acoustic source transducer and the acoustic receiving transducer being disposed in the cavity of the fluidic container and arranged in a pulse-echo configuration.

Another aspect of the disclosure includes the acoustic source transducer and the acoustic receiving transducer being disposed in the cavity of the fluidic container and arranged in a pitch-catch configuration.

Another aspect of the disclosure includes the acoustic receiving transducer being a flat surface.

Another aspect of the disclosure includes the acoustic receiving transducer being a curved surface.

Another aspect of the disclosure includes the acoustic receiving transducer being disposed on an opposite side of the workpiece from the acoustic source transducer.

Another aspect of the disclosure includes the acoustic receiving transducer being disposed in a second container that defines a cavity having an aperture that defines a peripheral portion, wherein the cavity contains acoustic transmission fluid, wherein a conformable membrane is sealably disposed about the peripheral portion of the aperture of the second container, wherein the membrane is disposed to sealably contain the acoustic transmission fluid within the second container, and wherein the conformable membrane is disposed to conform to a surface of a portion of the workpiece absent interposed fluid, and wherein the acoustic receiving transducer is disposed in the cavity of the second container and in contact with the acoustic transmission fluid, wherein the acoustic receiving transducer is disposed to monitor the residual acoustic wave that is transmitted through the workpiece in response to the first acoustic wave.

Another aspect of the disclosure includes the fluidic container and the second container being positional alignment devices that are disposed to arrange the acoustic source transducer in XY space relative to the acoustic receiving transducer.

Another aspect of the disclosure includes the peripheral portion of the aperture of the fluidic container including an outer sealing surface and an inner peripheral channel having a plurality of apertures that are fluidly connected to a controllable vacuum source, wherein the vacuum source is disposed to urge the membrane to conform to a portion of the workpiece without interposed air or fluid.

Another aspect of the disclosure includes the apparatus being portable.

Another aspect of the disclosure includes the peripheral portion of the aperture of the fluidic container including positional alignment devices.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which.

DETAILED DESCRIPTION

The components of the disclosed embodiments, as described and illustrated herein, may be arranged and designed in a variety of different configurations. Thus, the following detailed description is not intended to limit the scope of the disclosure, as claimed, but is merely representative of possible embodiments thereof. In addition, while numerous specific details are set forth in the following description in order to provide a thorough understanding of the embodiments disclosed herein, some embodiments can be practiced without these details. Moreover, for the purpose of clarity, certain technical material that is understood in the related art has not been described in detail in order to avoid obscuring the disclosure. Furthermore, the drawings are in simplified form and are not to precise scale. For purposes of convenience and clarity only, directional terms such as top, bottom, left, right, up, over, above, below, beneath, rear, and front, may be used with respect to the drawings. These and similar directional terms are not to be construed to limit the scope of the disclosure. Furthermore, the disclosure, as illustrated and described herein, may be practiced in the absence of an element that is not specifically disclosed herein.

Figure 1:
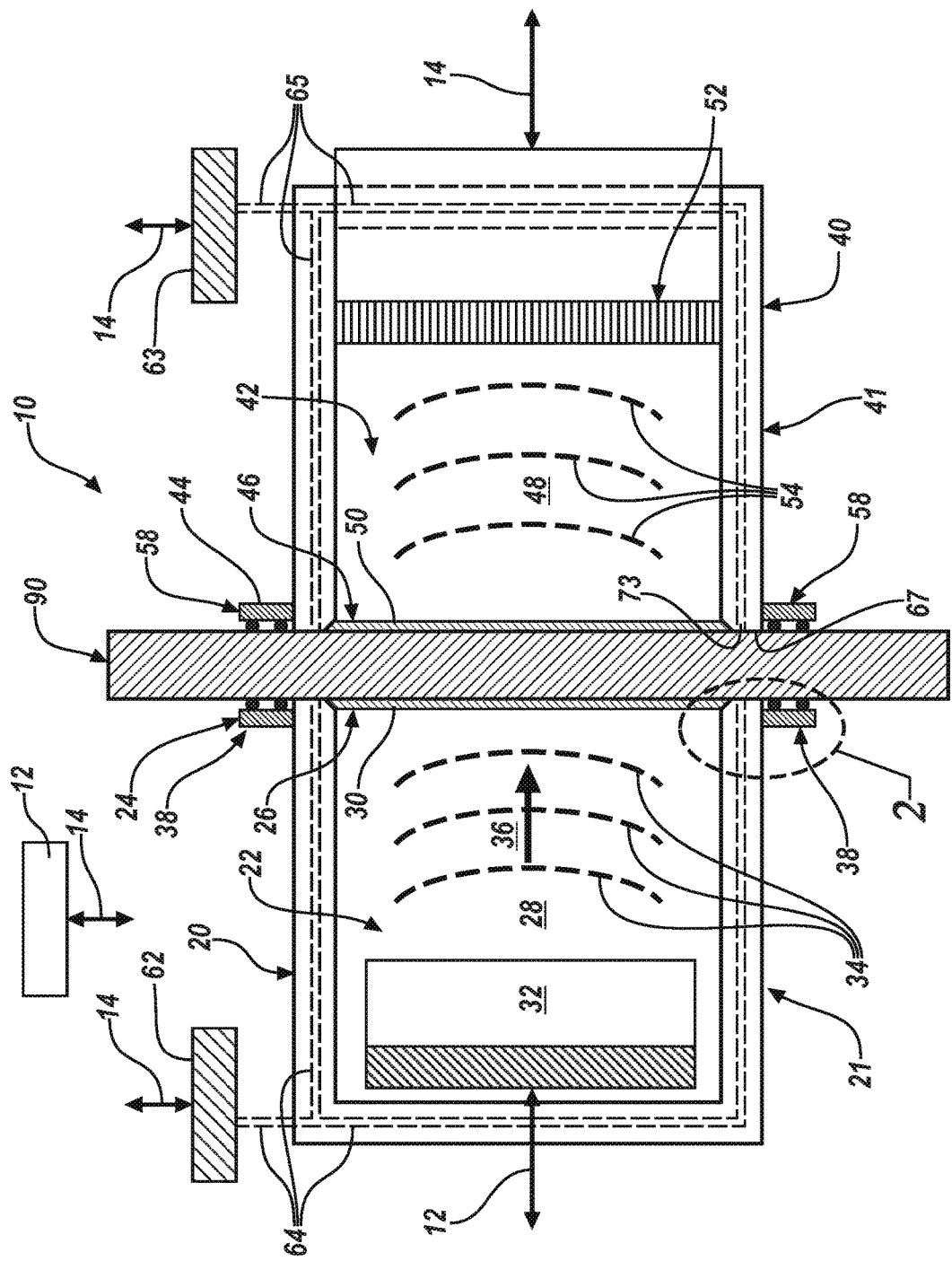
FIG. 1 schematically illustrates a side-view perspective of an embodiment of a two-sided, through-transmission acoustic monitoring device for in-situ monitoring of a workpiece, in accordance with the disclosure.

Referring to the drawings, wherein like reference numerals correspond to like or similar components throughout the several Figures, FIG. 1, consistent with embodiments disclosed herein, schematically illustrates a side-view perspective of an embodiment of an apparatus in the form of a two-sided, through-transmission acoustic monitoring device 10 for in-situ monitoring of all or a portion (as shown) of a workpiece 90 employing acoustic monitoring. The workpiece 90 is shown as a flat sheet of fabricated material having a uniform thickness, although the concepts described herein are not so limited. The workpiece 90 may be composed of a polymer, cast iron, steel, aluminum, copper, powdered metal or another material that may contain voids, delaminations, impurities or other surface or subsurface anomalies that may not be detected by visual inspection methods. Applications of the concepts described herein may be employed to inspect in-situ structural members that are deployed in various infrastructures, e.g., bridges, pavements, rail, building structures, water and gas pipelines, aerospace, e.g., inspection of composites, etc.

The monitoring device 10 in this embodiment is configured as a two-sided, through-transmission device that includes an acoustic sending unit 20 that includes an acoustic source transducer 32 that is disposed in a first fluidic container 21, and an acoustic receiving unit 40 that includes an acoustic receiving transducer 52 that is disposed in a second fluidic container 41. The first fluidic container 21 may be a suitable multi-dimensional shape, and includes a first internal cavity 22 that is open on one end at a first aperture 26 that is defined by a first periphery 24. The acoustic source transducer 32 is disposed in the first internal cavity 22 of the first fluidic container 21, preferably at an end that is opposite to the first aperture 26. The first internal cavity 22 of the first fluidic container 21 is filled with an acoustic transmission fluid 28 such that the acoustic source transducer 32 is immersed therein. The acoustic transmission fluid 28 may be a suitable acoustic transmission fluid. A first conformable membrane 30 is sealably disposed about the first periphery 24 of the first aperture 26 of the first fluidic container 21 such that the first conformable membrane 30 sealably contains the acoustic transmission fluid 28 within the first fluidic container 21. Preferably, the acoustic source transducer 32 is completely immersed in the acoustic transmission fluid 28 regardless of the spatial position or orientation of either the monitoring device 10 or the first fluidic container 21. A controller 12 is in communication with the acoustic source transducer 32 and the acoustic receiving transducer 52 to control operation thereof and analyze generated signals.

In this embodiment, the second fluidic container 41 includes a second internal cavity 42 that is open on one end at a second aperture 46 that is defined by a second periphery 44. In one embodiment, the design and shape of the second aperture 46 and the second periphery 44 are configured to be equivalent to and conform to the design and shape of the first aperture 26 and the first periphery 24, which permits the second fluidic container 41 to be advantageously arranged opposite to the first fluidic container 21 to effect monitoring. The first fluidic container 21 conforms to the workpiece 90 on its first side, and the second fluidic container 41 conforms to the workpiece 90 on its second side, in a complementary manner.

The second fluidic container 41 may be a suitable multi-dimensional shape, and includes a second internal cavity 42 that is open on one end at the second aperture 46 that is defined by the second periphery 44. The acoustic receiving transducer 52 is disposed in the second internal cavity 42 of the second fluidic container 41, preferably at an end that is opposite to the second aperture 46. The second internal cavity 42 of the second fluidic container 41 is filled with acoustic transmission fluid 48 such that the acoustic receiving transducer 52 is immersed therein. The acoustic transmission fluid 48 may be a suitable acoustic transmission fluid, and is preferably the same fluid as employed as the acoustic transmission fluid 28. A second conformable membrane 50 is sealably disposed about the periphery 44 of the second aperture 46 of the second fluidic container 41 such that the second conformable membrane 50 sealably contains the acoustic transmission fluid 48 within the second fluidic container 41. Preferably, the acoustic receiving transducer 52 is completely immersed in the acoustic transmission fluid 48 regardless of the spatial position or orientation of either the monitoring device 10 or the second fluidic container 41. The first and second conformable membranes 30, 50 may be fabricated from a suitable pliable material, including by way of non-limiting examples, latex rubber, silicone, etc.

Figure 2:
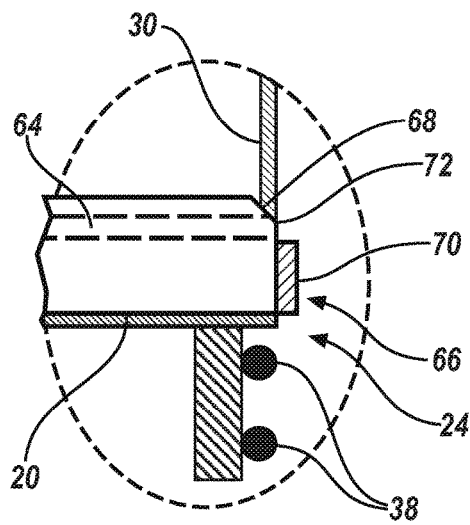
FIG. 2 schematically illustrates details of a portion of the side-view perspective of the two-sided, through-transmission acoustic monitoring device that is shown with reference to FIG. 1, in accordance with the disclosure.

The first fluidic container 21 includes a plurality of first positional alignment and joining devices 38, and the second fluidic container 41 includes a corresponding plurality of second positional alignment and joining devices 58. The first positional alignment and joining devices 38 are preferably disposed around the first periphery 24 of the first fluidic container 21 at the first aperture 26. In a similar fashion, the second positional alignment and joining devices 58 are preferably disposed around the second periphery 44 of the second fluidic container 41 at the second aperture 46. Each of the first and second positional alignment and joining devices 38, 58 preferably includes positional orientation encoders in the form of XY position encoders and joining devices. The XY position encoders are a suitable mechanical or electronic devices that are configured to determine spatial position to align the rotational position of the first fluidic container 21 with a corresponding rotational position of the second fluidic container 41. The joining devices are a suitable joining devices, e.g., permanent magnet devices that releasably join the first fluidic container 21 with the second fluidic container 41. These elements are shown with reference to FIG. 2.

Figure 3:
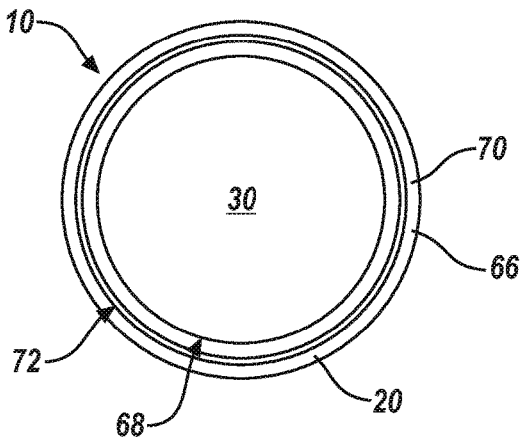
FIG. 3 schematically illustrates an end-view perspective of the two-sided, through-transmission acoustic monitoring device that is shown with reference to FIG. 1, in accordance with the disclosure.

The acoustic sending unit 20 preferably includes a pressure source 62 that is fluidly coupled via one or a plurality of channels 64 to one or a plurality of vacuum apertures 72 that are disposed on a face portion 66 of the first periphery 24 of the first fluidic container 21. The face portion 66 of the first periphery 24 preferably includes a flat surface having a face sealing gasket 70 and an inwardly tapered edge portion 68. The first conformable membrane 30 is preferably attached to the face portion 66 of the first periphery 24 to cover and enclose the first aperture 26 such that the inwardly tapered edge portion 68 is covered by the first conformable membrane 30. The vacuum aperture(s) 72 is fluidly connected to the face portion 66 of the first periphery 24 to permit air flow between an outer surface of the first conformable membrane 30 and the workpiece 90, with the workpiece 90 sealed against the acoustic sending unit 20 by a face sealing gasket 70 that is disposed on an outward portion of the face portion 66 of the first periphery 24. These elements are also shown with reference to FIG. 3, which schematically illustrates an end-view perspective of the acoustic sending unit 20 of the monitoring device 10.

The acoustic receiving unit 40 preferably includes a pressure source 63 that is fluidly coupled via one or a plurality of channels 65 to one or a plurality of vacuum apertures 73 that are disposed on a face portion 67 of the second periphery 44 of the second fluidic container 41. The face portion 67 of the second periphery 44 preferably includes a flat surface having a face sealing gasket and an inwardly tapered edge portion (not shown), which are analogous to the face sealing gasket 66 and inwardly tapered edge portion 68 of the acoustic sending unit 20. The second conformable membrane 50 is preferably attached to the face portion 66 of the second periphery 44 to cover and enclose the second aperture 46 such that the inwardly tapered edge portion is covered by the second conformable membrane 50. The vacuum aperture(s) 73 is fluidly connected to the face portion 67 of the second periphery 44 to permit air flow between an outer surface of the second conformable membrane 50 and the workpiece 90, with the workpiece 90 sealed against the acoustic receiving unit 40 by a face sealing gasket that is disposed on an outward portion of the face portion 67 of the second periphery 44.

In operation, when the acoustic sending unit 20 is positioned against the workpiece 90 and vacuum is applied by operation of the pressure source 62, the first conformable membrane 30 is advantageously drawn by the applied vacuum against a portion of the workpiece 90 that is covered by the face portion 66 of the first periphery 24 of the acoustic sending unit 20, thus causing the first conformable membrane 30 to conform to the surface of the workpiece 90 and provide a continuous fluidic coupling path from the acoustic source transducer 32 to the workpiece 90 via the first conformable membrane 30. As such, the first conformable membrane 30 is coupled to the workpiece 90 absent an interposed fluid or gel, and there is a fluidic acoustic coupling path from the acoustic source transducer 32 through the acoustic transmission fluid 48 and the first conformable membrane 30 to the workpiece 90, wherein the fluidic acoustic coupling path is uninterrupted by air. The acoustic source transducer 32 generates a source acoustic wave 34 in the direction 36 of the workpiece 90 in response to a command from the controller 12.

In a similar manner, the acoustic receiving unit 40 is positioned against the workpiece 90 and vacuum is applied by operation of the second pressure source 63, the second conformable membrane 50 is advantageously drawn by the vacuum against a portion of the workpiece 90 that is covered by the face portion 67 of the second periphery 44 of the acoustic receiving unit 40, thus causing the second conformable membrane 50 to conform to the surface of the workpiece 90 to provide a continuous fluidic coupling from the acoustic receiving transducer 52 to the workpiece 90 via the second conformable membrane 50. As such, the second conformable membrane 50 is coupled to the workpiece 90 absent an interposed fluid or gel, and there is a fluidic acoustic coupling path from the acoustic receiving transducer 52 through the acoustic transmission fluid 48 and the second conformable membrane 50 to the workpiece 90, wherein the fluidic acoustic coupling path is uninterrupted by air. This arrangement can permit the monitoring device 10 to operate effectively on a smooth surface of the workpiece 90 or an irregular surface of the workpiece 90. The acoustic receiving transducer 52 is disposed to detect and perceive a residual acoustic wave 54, which is based upon the source acoustic wave 34 after it has been in contact with the workpiece 90. The residual acoustic wave 54 and spatial positional information from the XY position encoders of the positional alignment and joining devices 58 are communicated to the controller 12.

The acoustic source transducer 52 can be a suitable transducer capable of generating and transmitting ultrasonic acoustic waves, and are piezoelectric devices in one embodiment. The acoustic receiving transducer 52 is an acoustography sensing system that includes acoustography film, camera, light source, etc.) in one embodiment. The acoustography sensing system includes a film that reacts to ultrasound by "developing;" thus enabling one to take acoustic scans without the need for mechanical scanning. Alternatively, the acoustic receiving transducer 52 may be a scanning type application, such as a phased array, C-scan, or "paint brush" type scan.

Figure 4:
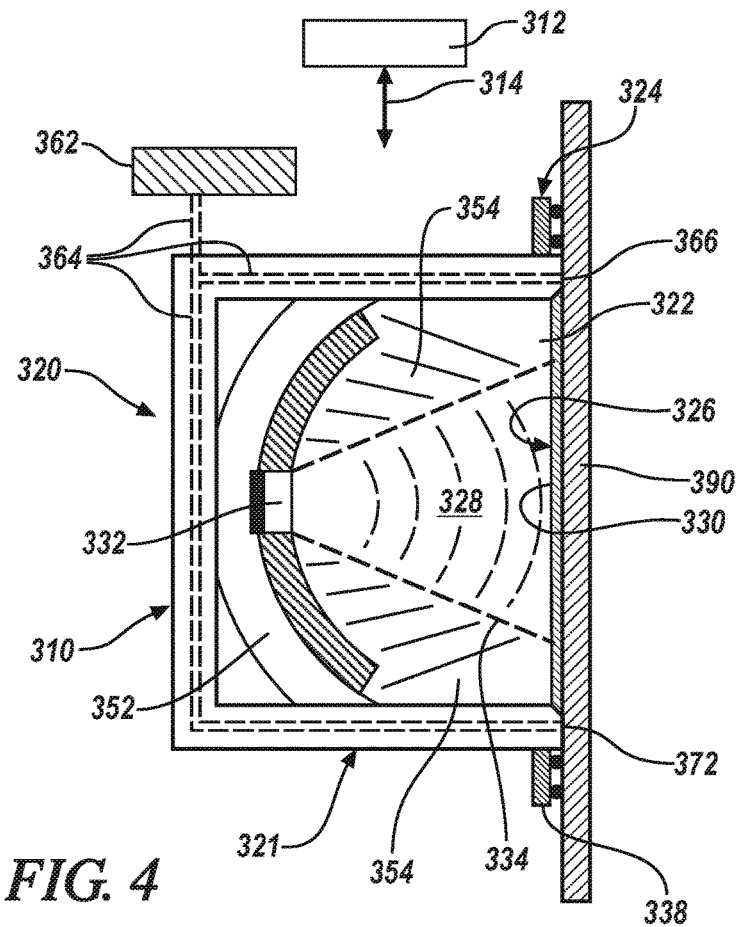
FIG. 4 schematically illustrates a side-view perspective of an embodiment of a one-sided reflective acoustic monitoring system that is disposed in a pulse-echo arrangement, in accordance with the disclosure.

FIG. 4 schematically illustrates a side-view perspective of an embodiment of a portable monitoring device 310 for in-situ monitoring of a workpiece employing a one-sided reflective acoustic monitoring system that is disposed in a pulse-echo arrangement. The pulse-echo arrangement includes the acoustic source transducer and the acoustic receiving transducer being disposed in a common cavity of a fluidic container, with the sending and receiving of the acoustic wave disposed in the same sensor unit. The sensor can include an acoustic source embedded in an acoustography film, or a multi-element transducer operating in pulse-echo mode where it sends and receives an acoustic wave.

The sending and receiving functions can be accomplished by a single sensor that is operating in a send/receive mode, or by two or more sensors operating in a single unit. The monitoring device 310 includes an acoustic sending/receiving unit 320 that includes an acoustic source transducer 332 and an acoustic receiving transducer 352 that are both disposed in a common fluidic container 321. The fluidic container 321 may be a suitable multi-dimensional shape, and includes an internal cavity 222 that is open on one end at an aperture 326 that is defined by a periphery 324. The acoustic source transducer 332 is centrally disposed in the internal cavity 322 of the fluidic container 321, preferably at an end that is opposite to the aperture 326. The internal cavity 322 is filled with an acoustic transmission fluid 328 such that the acoustic source transducer 332 is immersed therein. The acoustic transmission fluid 328 may be a suitable acoustic transmission fluid. A conformable membrane 330 is sealably disposed about the periphery 324 of the aperture 326 of the fluidic container 321 such that the conformable membrane 330 sealably contains the acoustic transmission fluid 328 within the fluidic container 321. Preferably, the acoustic source transducer 332 is completely immersed in the acoustic transmission fluid 328 regardless of the spatial position or orientation of the monitoring device 310, with a face portion of the acoustic source transducer 332 immersed under operating conditions. Operation of the acoustic source transducer 332 and the acoustic receiving transducer 352 is controlled by a controller 312 via a communication link 314.

The acoustic receiving transducer 352 may have a curved surface. By way of a non-limiting example, the acoustic receiving transducer 352 may be configured in the shape of a parabola with the acoustic source transducer 332 disposed at its vertex, as shown. Alternatively, the acoustic receiving transducer 352 may be configured in the shape of a partial cylinder, analogous to a half-pipe, with the acoustic source transducer 332 disposed at its base. In one embodiment, the partial cylinder may have a cross-sectional shape that is circular. Alternatively, the partial cylinder may have a cross-sectional shape that is parabolic. Preferably, the acoustic receiving transducer 352 is completely immersed in the acoustic transmission fluid 328 regardless of the shape, position or orientation of the monitoring device 310. The conformable membrane 330 may be fabricated from a suitable pliable material, including by way of non-limiting examples, latex rubber, silicone, etc.

The fluidic container 321 includes a plurality of positional alignment and joining devices 338. The positional alignment and joining devices 338 are preferably disposed around the periphery 324 of the fluidic container 321 at the aperture 326. Each of the positional alignment and joining devices 338 preferably includes positional orientation encoders in the form of XY position encoders. The XY position encoders are suitable mechanical or electronic devices that are configured to determine a spatial position. The fluidic container 321 preferably includes a pressure source 362 that is fluidly coupled via one or a plurality of channels 364 to one or a plurality of vacuum apertures 372 that are disposed on a face portion 366 of the periphery 324 of the fluidic container 321. The face portion 366 of the periphery 324 preferably includes a flat surface having a face sealing gasket and an inwardly tapered edge portion (not shown). The conformable membrane 330 is preferably attached to the face portion 366 of the periphery 324 to cover and enclose the aperture 326 such that the inwardly tapered edge portion is covered by the conformable membrane 330. The vacuum aperture(s) 372 is fluidly connected to the face portion 366 of the periphery 324 to permit air flow between an outer surface of the conformable membrane 330 and the workpiece 390, with the workpiece 390 being a sealed face sealing gasket 70 that is disposed on an outward portion of the face portion 366 of the periphery 324.

A continuous fluidic coupling path is provided from the acoustic source transducer 332 via the acoustic transmission fluid 348 and the conformable membrane 330 to the workpiece 390, and from the workpiece 390 to the acoustic receiving transducer 352 via the acoustic transmission fluid 348 and the conformable membrane 330. As such, the conformable membrane 330 is coupled to the workpiece 390 absent an interposed fluid or gel, and there is a fluidic acoustic coupling path from the acoustic source transducer 332 through the acoustic transmission fluid 348 and the conformable membrane 330 to the workpiece 390, wherein the fluidic acoustic coupling path is uninterrupted by air.

In operation, when the acoustic sending unit 320 is positioned against the workpiece 390 and vacuum is applied by operation of the pressure source 362, the conformable membrane 330 is advantageously drawn by the applied vacuum against a portion of the workpiece 390 that is covered by the face portion 366 of the periphery 324, thus causing the conformable membrane 330 to conform to the surface of the workpiece 390 to provide a continuous fluidic coupling from the acoustic source transducer 332 to the workpiece 390 via the conformable membrane 330. This arrangement can permit the monitoring device 310 to operate effectively on a smooth surface of the workpiece 390 or an irregular surface of the workpiece 390. In operation, the acoustic source transducer 332 generates a source acoustic wave 334 in the direction of the workpiece 390 in response to a command from the controller 312. The acoustic receiving transducer 352 is disposed to detect and perceive a residual acoustic wave 354, which is based upon the source acoustic wave 334 after it has been in contact with the workpiece 390. The residual acoustic wave 354 and spatial position information from the XY position encoders of the positional alignment and joining devices 338 are communicated to the controller 312.

Figure 5:
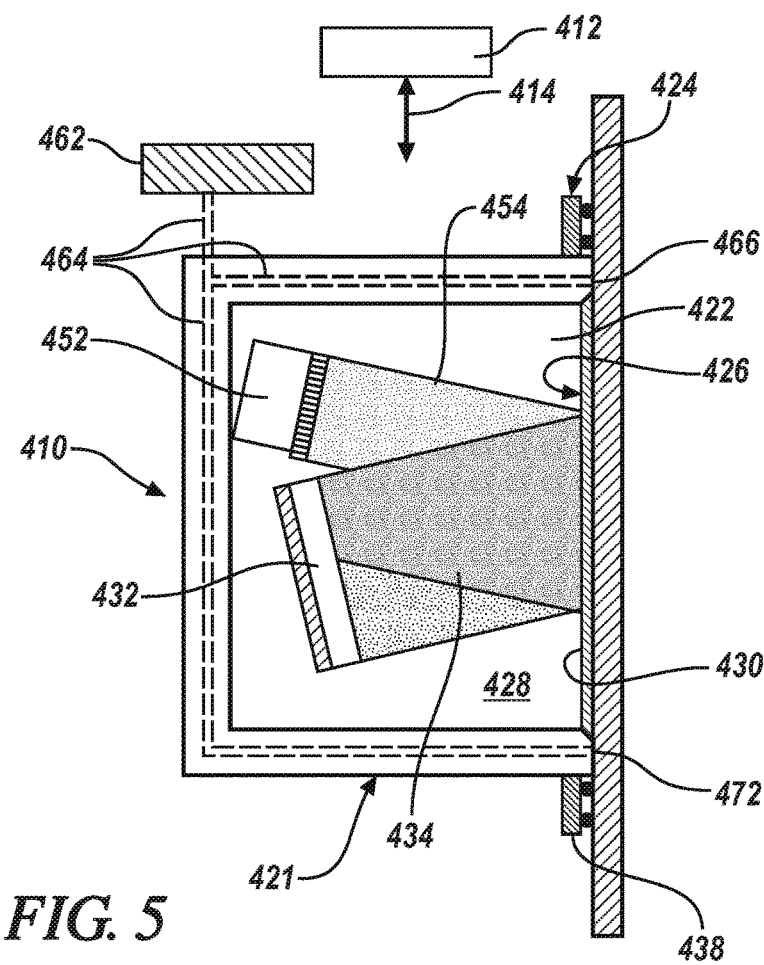
FIG. 5 schematically illustrates a side-view perspective of an embodiment of a one-sided reflective acoustic monitoring system that is disposed in a pitch-catch arrangement, in accordance with the disclosure.

FIG. 5 schematically illustrates a side-view perspective of an embodiment of a portable monitoring device for in-situ monitoring of a workpiece employing a one-sided reflective acoustic monitoring system that is disposed in a pitch-catch arrangement, wherein the sending and receiving transducers are oriented at an angle with respect to each other to accommodate detection of the acoustic wave.

The monitoring device 410 includes an acoustic sending/receiving unit 420 that includes an acoustic source transducer 432 and an acoustic receiving transducer 252 that are both disposed in a common fluidic container 421. In the pitch-catch arrangement, the acoustic source transducer 432 is offset from the acoustic receiving transducer 452 in the fluidic container 421 such that the acoustic receiving transducer 452 receives ultrasonic waves that are emitted by the acoustic source transducer 432 and reflected by the workpiece 490. The fluidic container 421 may be a suitable multi-dimensional shape, and includes an internal cavity 422 that is open on one end at an aperture 426 that is defined by a periphery 424. The acoustic source transducer 432 is disposed in the internal cavity 422 of the fluidic container 421, preferably at an end that is opposite to the aperture 426. The internal cavity 422 is filled with an acoustic transmission fluid 428 such that the acoustic source transducer 432 is immersed therein. The acoustic transmission fluid 428 may be a suitable acoustic transmission fluid. A conformable membrane 430 is sealably disposed about the periphery 424 of the aperture 426 of the fluidic container 421 such that the conformable membrane 430 sealably contains the acoustic transmission fluid 428 within the fluidic container 421. Preferably, the acoustic source transducer 432 and the acoustic receiving transducer 452 are completely immersed in the acoustic transmission fluid 428 regardless of the spatial position or orientation of the monitoring device 410. Operation of the acoustic source transducer 432 and the acoustic receiving transducer 452 is controlled by controller 412 via a communication link 414. The acoustic receiving transducer 452 is arranged as a flat surface that is disposed in the internal cavity 422, preferably offset from the acoustic source transducer 432. The conformable membrane 430 may be fabricated from a suitable pliable material, including by way of non-limiting examples, latex rubber, silicone, etc.

The fluidic container 421 includes a plurality of positional alignment and joining devices 438. The positional alignment and joining devices 438 are preferably disposed around the periphery 424 of the fluidic container 421 at the aperture 426. Each of the positional alignment and joining devices 438 preferably includes positional orientation encoders in the form of XY position encoders. The XY position encoders are a suitable mechanical or electronic devices that are configured to determine a spatial position.

The fluidic container 421 preferably includes a pressure source 462 that is fluidly coupled via one or a plurality of channels 464 to one or a plurality of vacuum apertures 472 that are disposed on a face portion 466 of the periphery 424 of the fluidic container 421. The face portion 466 of the periphery 424 preferably includes a flat surface having a face sealing gasket and an inwardly tapered edge portion (not shown). The conformable membrane 430 is preferably attached to the face portion 466 of the periphery 424 to cover and enclose the aperture 426 such that the inwardly tapered edge portion is covered by the conformable membrane 430.

The vacuum aperture(s) 472 is fluidly connected to the face portion 466 of the periphery 424 to permit air flow between an outer surface of the conformable membrane 430 and the workpiece 490, with the workpiece 490 being a sealed face sealing gasket 470 that is disposed on an outward portion of the face portion 466 of the periphery 424.

A continuous fluidic coupling path is provided from the acoustic source transducer 432 via the acoustic transmission fluid 448 and the conformable membrane 430 to the workpiece 490, and from the workpiece 490 to the acoustic receiving transducer 452 via the acoustic transmission fluid 448 and the conformable membrane 430. As such, the conformable membrane 430 is coupled to the workpiece 490 absent an interposed fluid or gel, and there is a fluidic acoustic coupling path from the acoustic source transducer 432 through the acoustic transmission fluid 348 and the conformable membrane 430 to the workpiece 490, wherein the fluidic acoustic coupling path is uninterrupted by air.

In operation, when the acoustic sending unit 420 is positioned against the workpiece 490 and vacuum is applied by operation of the pressure source 462, the conformable membrane 430 is advantageously drawn by the applied vacuum against a portion of the workpiece 490 that is covered by the face portion 466 of the periphery 424, thus causing the conformable membrane 430 to conform to the surface of the workpiece 490 to provide a continuous fluidic coupling from the acoustic source transducer 432 to the workpiece 490 via the conformable membrane 430. This arrangement can permit the monitoring device 410 to operate effectively on a smooth surface of the workpiece 490 or an irregular surface of the workpiece 490. In operation, the acoustic source transducer 432 generates a source acoustic wave 434 in the direction of the workpiece 490 in response to a command from the controller 412. The acoustic receiving transducer 452 is disposed to detect and perceive a residual acoustic wave 454, which is based upon the source acoustic wave 434 after it has been in contact with the workpiece 490. The residual acoustic wave 454 and spatial position information from the XY position encoders of the positional alignment and joining devices 338 are communicated to the controller 412.

Figure 6:
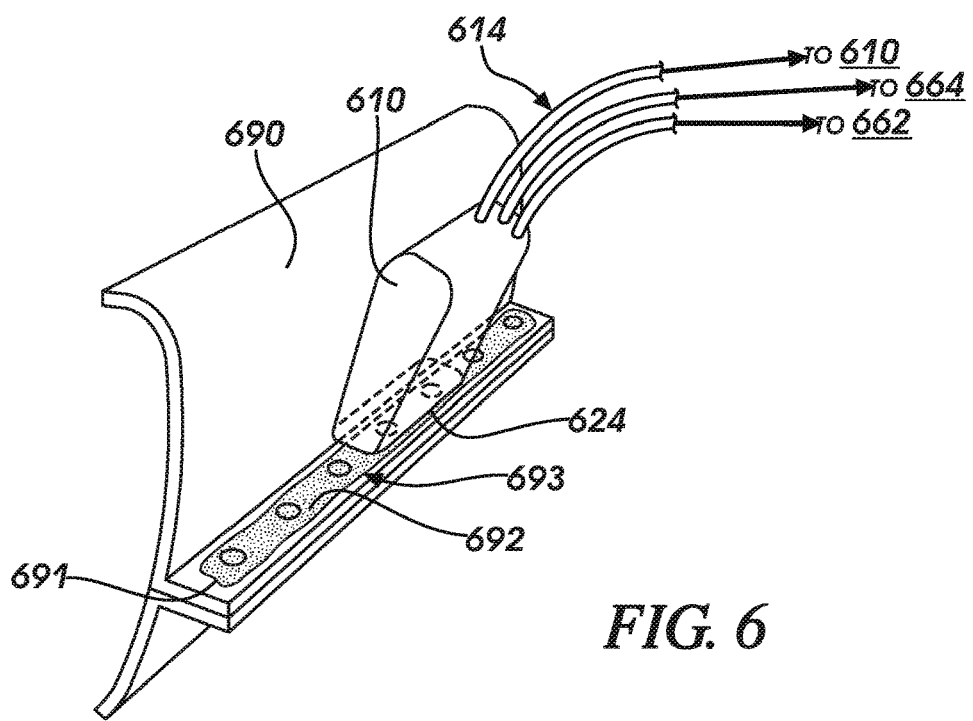
FIG. 6 illustrates an isometric perspective of an embodiment of a portable monitoring device for in-situ monitoring of a workpiece employing an embodiment of the one-sided reflective acoustic monitoring system described herein, in accordance with the disclosure.

FIG. 6 illustrates an isometric perspective of an embodiment of a portable monitoring device 610 for in-situ monitoring of a workpiece 690, wherein the portable monitoring device 610 includes a one-sided reflective acoustic monitoring system including a periphery 624 that defines an aperture that is covered and enclosed by a conformable membrane (not shown) such as is described herein with reference to the embodiments associated with FIG. 4 and FIG. 5. The workpiece 690 includes a flange portion 691 having a spot weld 692 and an adhesive bonding portion 693. The portable monitoring device 610 includes a handheld portion have a plurality of power, signal and pressure communication lines. These include a vacuum line 662 that couples a pressure source to an area between the conformable membrane on the portable monitoring device 610 and a portion of the workpiece 690. These include a control line 664 that is connected between the controller and an acoustic source transducer (not shown) that is disposed in the portable monitoring device 610. These also include a data link 614 that is connected between the controller and an acoustic receiving transducer (not shown) that is disposed in the portable monitoring device 610. A continuous fluidic coupling path is provided from the acoustic source transducer via the acoustic transmission fluid and the conformable membrane to the workpiece 690, and from the workpiece 690 to the acoustic receiving transducer via the acoustic transmission fluid and the conformable membrane. As such, the conformable membrane is coupled to the workpiece 690 absent an interposed fluid or gel, and there is a fluidic acoustic coupling path from the acoustic source transducer through the acoustic transmission fluid and the conformable membrane to the workpiece 690, wherein the fluidic acoustic coupling path is uninterrupted by air.

The term "controller" and related terms such as control module, module, control, control unit, processor and similar terms refer to one or various combinations of Application Specific Integrated Circuit(s) (ASIC), electronic circuit(s), central processing unit(s), e.g., microprocessor(s) and associated non-transitory memory component(s) in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean controller-executable instruction sets including calibrations and look-up tables. Each controller executes control routine(s) to provide desired functions. Routines may be executed at regular intervals, for example each 100 microseconds during ongoing operation. Alternatively, routines may be executed in response to occurrence of a triggering event. Communication between controllers, and communication between controllers, actuators and/or sensors may be accomplished using a direct wired point-to-point link, a networked communication bus link, a wireless link or another suitable communication link, and is indicated by link 14. Communication includes exchanging data signals in suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to a physically discernible indicator that conveys information, and may be a suitable waveform (e.g., electrical, optical, magnetic, mechanical or electromagnetic), such as DC, AC, sinusoidal-wave, triangular-wave, square-wave, vibration, and the like, that is capable of traveling through a medium.

In operation, embodiments of the apparatus for in-situ monitoring of a workpiece that are described herein can be employed to characterize acoustic properties of a workpiece to be inspected and determine desired defect detection resolution, which can include determining acoustic attenuations/velocities. Furthermore, acoustic properties can be employed to control limits on thickness of the part. Furthermore quality standards can be developed that define a resolution for fault detection. This can include selecting an appropriate frequency or range. As appreciated, higher frequencies can be more attenuative, but allow for higher resolution in fault detection. Furthermore higher frequency sources generally emit less power. When employed, the acoustography detection system may be more sensitive to some frequencies than others. The concepts described herein can extend the applicability of acoustography to arrangement where a workpiece cannot be immersed in a fluid, and also operate without requiring a fluid or gel couplant. Acoustography has been shown to have faster processing times than ultrasonic scans.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

What is claimed is:

1. An apparatus for in-situ monitoring of a workpiece, comprising:
    a fluidic container defining a cavity and having a peripheral portion that defines an aperture;
    the fluidic container containing an acoustic transmission fluid;
    a conformable membrane sealably disposed about the peripheral portion of the aperture of the fluidic container, wherein the membrane is disposed to sealably contain the acoustic transmission fluid within the fluidic container, and wherein the conformable membrane is disposed to conform to a surface of a portion of the workpiece;
    an acoustic source transducer disposed in the cavity of the fluidic container and in contact with the acoustic transmission fluid, wherein the acoustic source transducer is disposed to generate a first acoustic wave in the direction of the workpiece; and
    an acoustic receiving transducer, wherein the acoustic receiving transducer is disposed to monitor a residual acoustic wave that is reflected from the workpiece in response to the first acoustic wave.

2. The apparatus of claim 1, wherein the acoustic receiving transducer comprises an acoustography sensor.

3. The apparatus of claim 1, wherein the acoustic receiving transducer comprises a multi-element acoustic receiving transducer.

4. The apparatus of claim 1, wherein the acoustic receiving transducer is disposed in the same fluidic container as the acoustic sending unit.

5. The apparatus of claim 4, wherein the acoustic source transducer and the acoustic receiving transducer are disposed in the cavity of the fluidic container and arranged in a pulse-echo configuration.

6. The apparatus of claim 4, wherein the acoustic source transducer and the acoustic receiving transducer are disposed in the cavity of the fluidic container and arranged in a pitch-catch configuration.

7. The apparatus of claim 1, wherein the acoustic receiving transducer comprises a flat surface.

8. The apparatus of claim 1, wherein the acoustic receiving transducer comprises a curved surface.

9. The apparatus of claim 1, wherein the acoustic receiving transducer is disposed on an opposite side of the workpiece from the acoustic source transducer.

10. The apparatus of claim 9, wherein the acoustic receiving transducer is disposed in a second container that defines a cavity having an aperture that defines a peripheral portion, wherein the cavity contains acoustic transmission fluid, wherein a conformable membrane is sealably disposed about the peripheral portion of the aperture of the second container, wherein the membrane is disposed to sealably contain the acoustic transmission fluid within the second container, and wherein the conformable membrane is disposed to conform to a surface of a portion of the workpiece absent an interposed fluid, and wherein the acoustic receiving transducer is disposed in the cavity of the second container and in contact with the acoustic transmission fluid, wherein the acoustic receiving transducer is disposed to monitor the residual acoustic wave that is transmitted through the workpiece in response to the first acoustic wave.

11. The apparatus of claim 10, wherein the fluidic container and the second container further comprise positional alignment devices that are disposed to arrange the acoustic source transducer in XY space relative to the acoustic receiving transducer.

12. The apparatus of claim 1, wherein the peripheral portion of the aperture of the fluidic container includes an outer sealing surface and an inner peripheral channel that is fluidly connected to a controllable vacuum source, wherein the vacuum source is disposed to urge the membrane to conform to a portion of the workpiece without interposed air or fluid.

13. The apparatus of claim 12, wherein the inner peripheral channel includes a plurality of apertures that are fluidly connected to the controllable vacuum source.

14. The apparatus of claim 1, wherein the conformable membrane is disposed to conform to a surface of a portion of the workpiece absent an interposed fluid.

15. The apparatus of claim 1, wherein the peripheral portion of the aperture of the fluidic container includes positional alignment devices.

16. A portable apparatus for in-situ monitoring of a workpiece, comprising:
    a fluidic container defining a cavity and having a peripheral portion that defines an aperture;
    the fluidic container containing an acoustic transmission fluid;
    a conformable membrane sealably disposed about the peripheral portion of the aperture of the fluidic container, wherein the membrane is disposed to sealably contain the acoustic transmission fluid within the fluidic container, and wherein the conformable membrane is disposed to conform to a surface of a portion of the workpiece, wherein the peripheral portion of the aperture of the fluidic container includes an outer sealing surface and a plurality of apertures that are fluidly connected to a vacuum source;
    an acoustic source transducer disposed in the cavity of the fluidic container and in contact with the acoustic transmission fluid, wherein the acoustic source transducer is disposed to generate a first acoustic wave in the direction of the workpiece; and
    an acoustic receiving transducer disposed in the cavity of the fluidic container and in contact with the acoustic transmission fluid, wherein the acoustic receiving transducer is disposed to monitor a residual acoustic wave that is reflected from the workpiece in response to the first acoustic wave;
    wherein the vacuum source is disposed to evacuate air between the membrane and the workpiece via the plurality of apertures to urge the membrane to conform to the workpiece without interposed air or fluid.

17. The apparatus of claim 16, wherein the acoustic receiving transducer comprises an acoustography sensor.

18. The apparatus of claim 16, wherein the acoustic source transducer and the acoustic receiving transducer are disposed in the cavity of the fluidic container and arranged one of a pulse-echo configuration or a pitch-catch configuration.

19. The apparatus of claim 16, wherein the acoustic receiving transducer comprises a parabolic surface.

20. The apparatus of claim 16, wherein the wherein the conformable membrane is disposed to conform to a surface of a portion of the workpiece absent an interposed fluid.

* * * * *